US011045636B1

(12) United States Patent
Watza et al.

(10) Patent No.: US 11,045,636 B1
(45) Date of Patent: Jun. 29, 2021

(54) DEVICE FOR SIMPLE ATTACHMENT AND REMOVAL OF FLOW DURING INTUBATION

(71) Applicants: Keith Joseph Watza, Oakland, MI (US); Zachary William Murdock, Los Angeles, CA (US); Samuel Jacob Luethy, Chesterfield, MO (US); Cody Matthew O'Cain, Charlottseville, VA (US)

(72) Inventors: Keith Joseph Watza, Oakland, MI (US); Zachary William Murdock, Los Angeles, CA (US); Samuel Jacob Luethy, Chesterfield, MO (US); Cody Matthew O'Cain, Charlottseville, VA (US)

(*) Notice: Subject to any disclaimer, the term of this patent is extended or adjusted under 35 U.S.C. 154(b) by 573 days.

(21) Appl. No.: 15/955,442

(22) Filed: Apr. 17, 2018

Related U.S. Application Data

(60) Provisional application No. 62/486,731, filed on Apr. 18, 2017.

(51) Int. Cl.
| | |
|---|---|
| *A61M 39/10* | (2006.01) |
| *A61M 16/04* | (2006.01) |
| *A61B 1/00* | (2006.01) |
| *A61J 15/00* | (2006.01) |

(52) U.S. Cl.
CPC .... *A61M 39/1011* (2013.01); *A61M 16/0461* (2013.01); *A61M 16/0463* (2013.01); *A61M 16/0488* (2013.01); *A61B 1/00147* (2013.01); *A61J 15/0003* (2013.01); *A61M 2039/1016* (2013.01)

(58) Field of Classification Search
CPC .......... A61M 16/0461; A61M 16/0463; A61M 16/0488; A61M 16/0672; A61M 16/0875; A61M 39/1011; A61M 2039/1016; A61M 2039/1027; A61J 15/0003; A61B 1/00147
See application file for complete search history.

(56) References Cited

U.S. PATENT DOCUMENTS

| | | | | |
|---|---|---|---|---|
| 4,123,091 A | * | 10/1978 | Cosentino | F16L 37/0847 285/39 |
| 4,388,076 A | * | 6/1983 | Waters | A61M 39/10 128/912 |
| 4,852,564 A | * | 8/1989 | Sheridan | A61M 16/04 128/202.27 |
| 5,024,220 A | * | 6/1991 | Holmgreen | A61M 16/0463 128/200.26 |

(Continued)

*Primary Examiner* — Valerie L Woodward
(74) *Attorney, Agent, or Firm* — Young Basile Hanlon & MacFarlane, P.C.

(57) ABSTRACT

An apparatus for selectively coupling a first tube and a second tube allows easy separation and connection of tubing in cases of accidental or forceful removal of the tube. A first connecting member and a second connecting member can be easily connected and disconnected as needed to prevent and allow fluid flow to and from a patient. The apparatus can be applied to prevent the accidental removal of patients undergoing extended treatments involving tubes entering the body in the clinical, geriatric, or other care settings. The apparatus also allows for the purposeful detachment and sealing of tubes entering the body to allow for increased patient mobility.

20 Claims, 21 Drawing Sheets

(56) References Cited

U.S. PATENT DOCUMENTS

| | | | | |
|---|---|---|---|---|
| 5,645,539 A * | 7/1997 | Solomon | ........... | A61M 39/0247 |
| | | | | 285/261 |
| 5,984,378 A * | 11/1999 | Ostrander | ........... | F16L 37/0985 |
| | | | | 285/319 |
| 7,390,028 B2 * | 6/2008 | Blazek | ............... | A61M 39/1011 |
| | | | | 285/242 |
| 2014/0378907 A1 * | 12/2014 | Liu | ..................... | A61J 15/0057 |
| | | | | 604/178 |
| 2018/0369558 A1 * | 12/2018 | Nordquist | ........... | A61M 1/0023 |

\* cited by examiner

DEVICE FOR SIMPLE ATTACHMENT AND REMOVAL OF FLOW DURING INTUBATION

CROSS-REFERENCE TO RELATED APPLICATION(S)

This application claims priority to and the benefit of U.S. Provisional Application Patent Ser. No. 62/486,731, filed Apr. 18, 2017, the entire disclosure of which is hereby incorporated by reference.

TECHNICAL FIELD

The present invention relates to devices for medical intubation of a patient.

BACKGROUND

A nasogastric intubation is the process of inserting a tube through a patients' nasal cavity down to the stomach in order to remove gas and other gastric secretions from the stomach. The tubes can be used to also provide much needed nutrition, water, and medication to the patient. Often the tubes that are inserted into the patient can be accidentally dislodged or forcefully removed by a frightened patient. In such cases re-establishing the tubing can prove to be difficult, endangering the patient. Furthermore, the removal of the in vivo tubing can cause bodily harm to the patient.

SUMMARY

Disclosed herein are methods and apparatuses for selectively coupling a first tube to a second tube. An apparatus for selectively coupling a first tube to a second tube may include a first connecting member including a first channel axially extending through the first connecting member. The first channel may have a proximal end and a distal end. A portion of first channel may be adapted to attachably receive the first tube. A second connecting member may be selectively couplable to the first connecting member. A second channel may axially extend through the second connecting member. The second channel may have a proximal end second channel and a distal end. A portion of the second channel may be adapted to attachably receive the second tube. The second connecting member may include a recess having an interior profile corresponding to an exterior profile of a portion of the first connecting member. Coupling the second connecting member to the first connecting member may cause axial alignment of the proximal end of first channel and the proximal end of the second channel.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
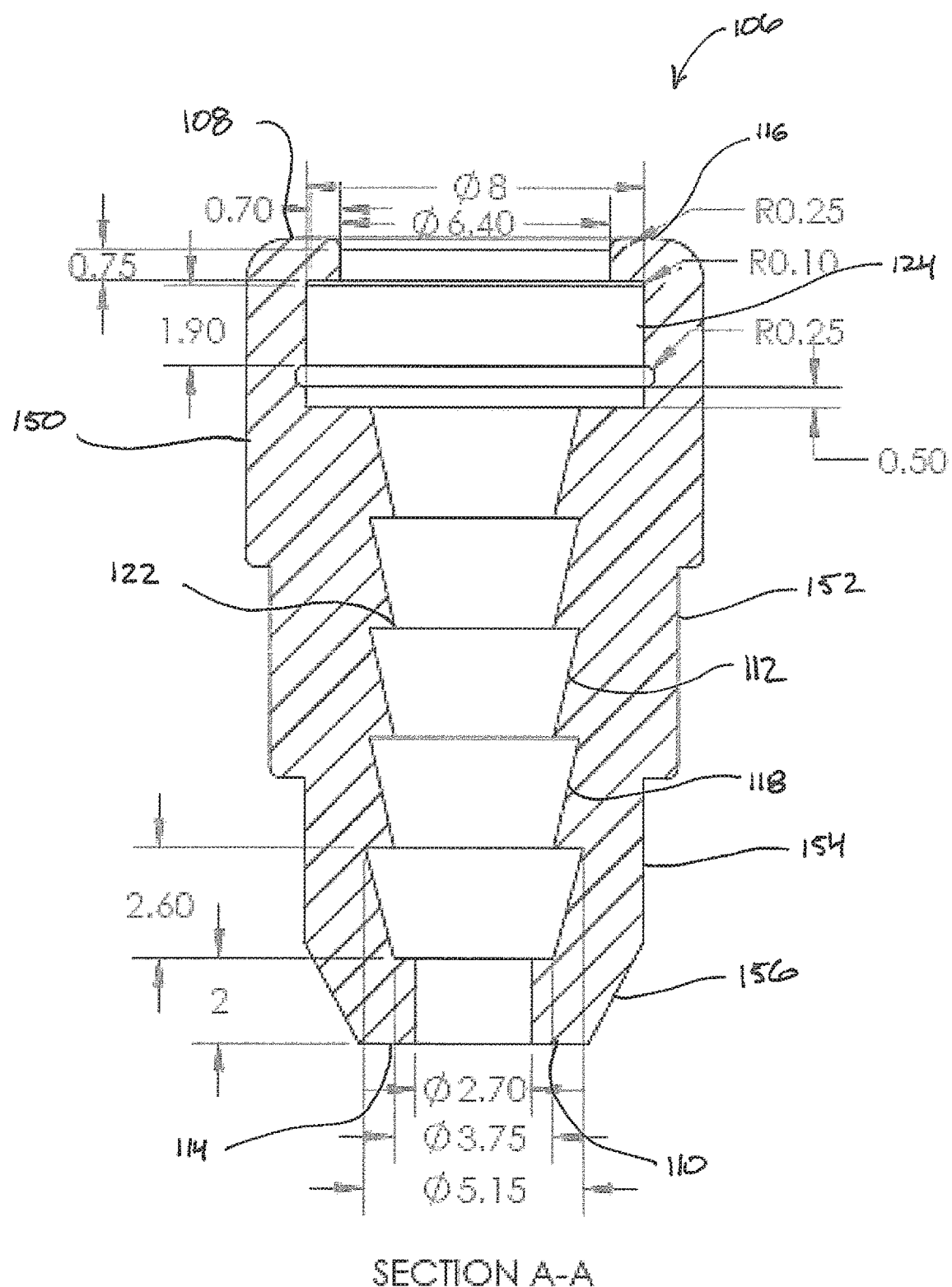
FIG. 1 is a side view partly in section showing an embodiment of a first connecting member of an apparatus for selectively coupling a first tube to a second tube.
Figure 2:
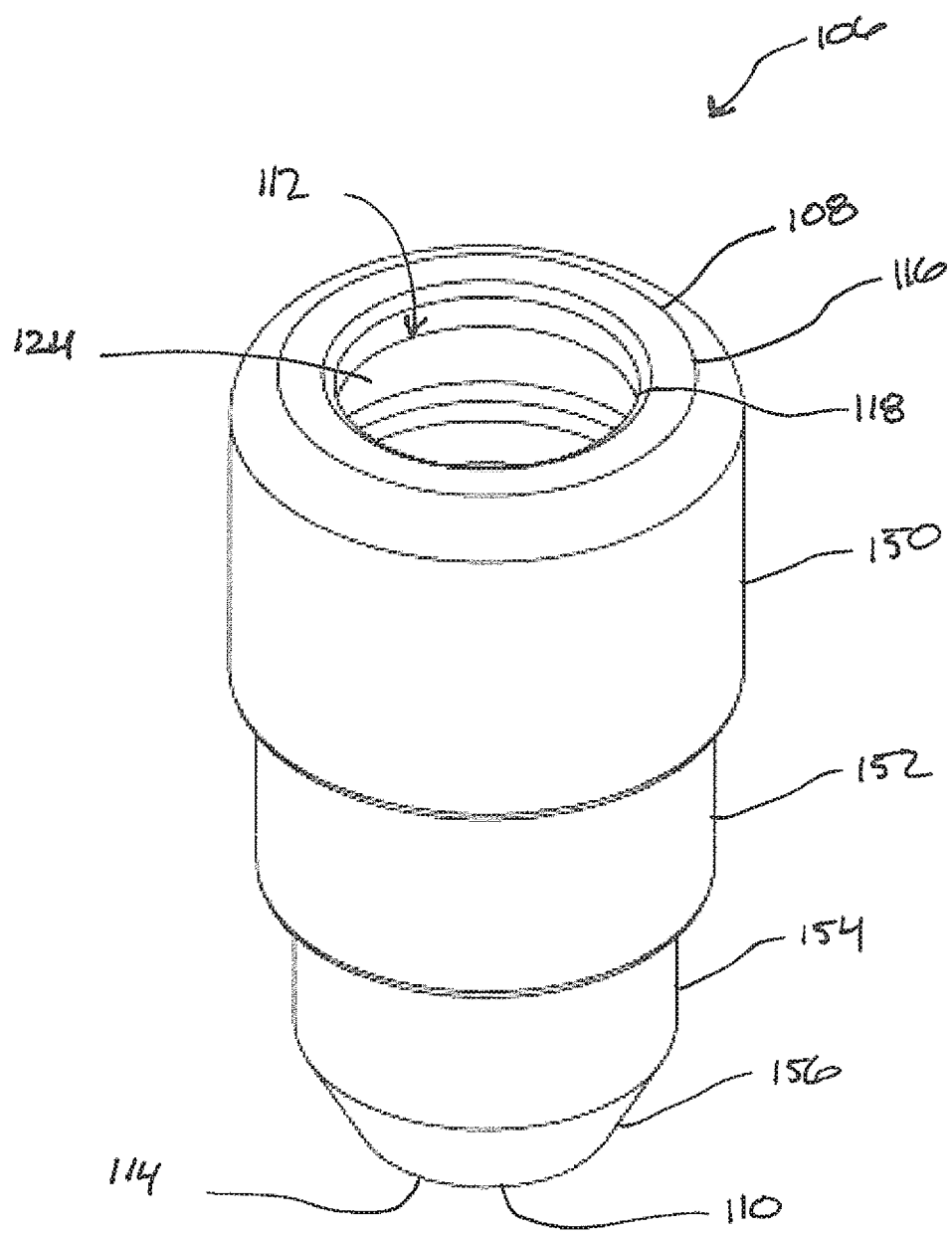
FIG. 2 is an elevated side view of the first connecting member of FIG. 1.
Figure 3:
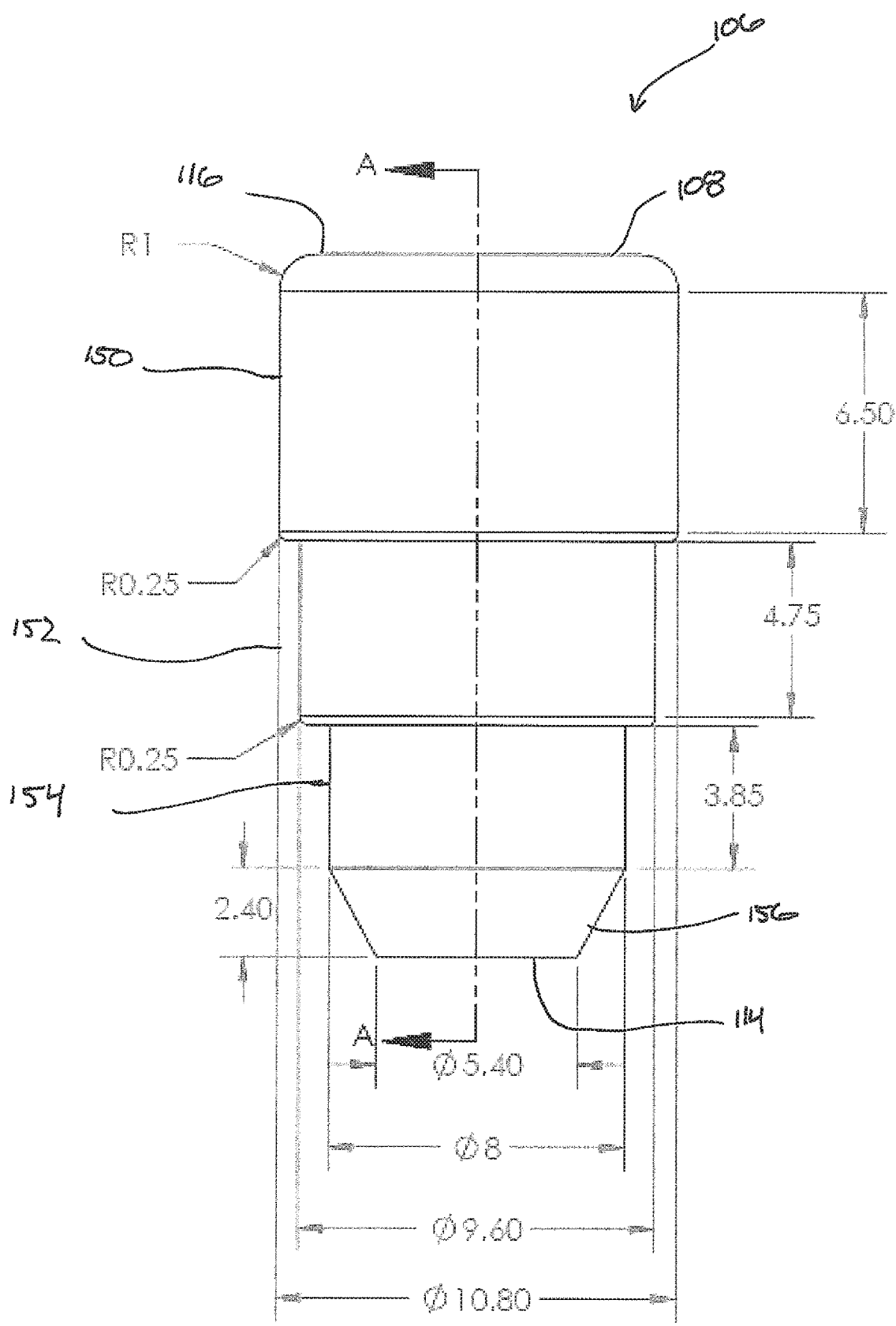
FIG. 3 is a side view of the first connecting member of FIG. 1.
Figure 4:
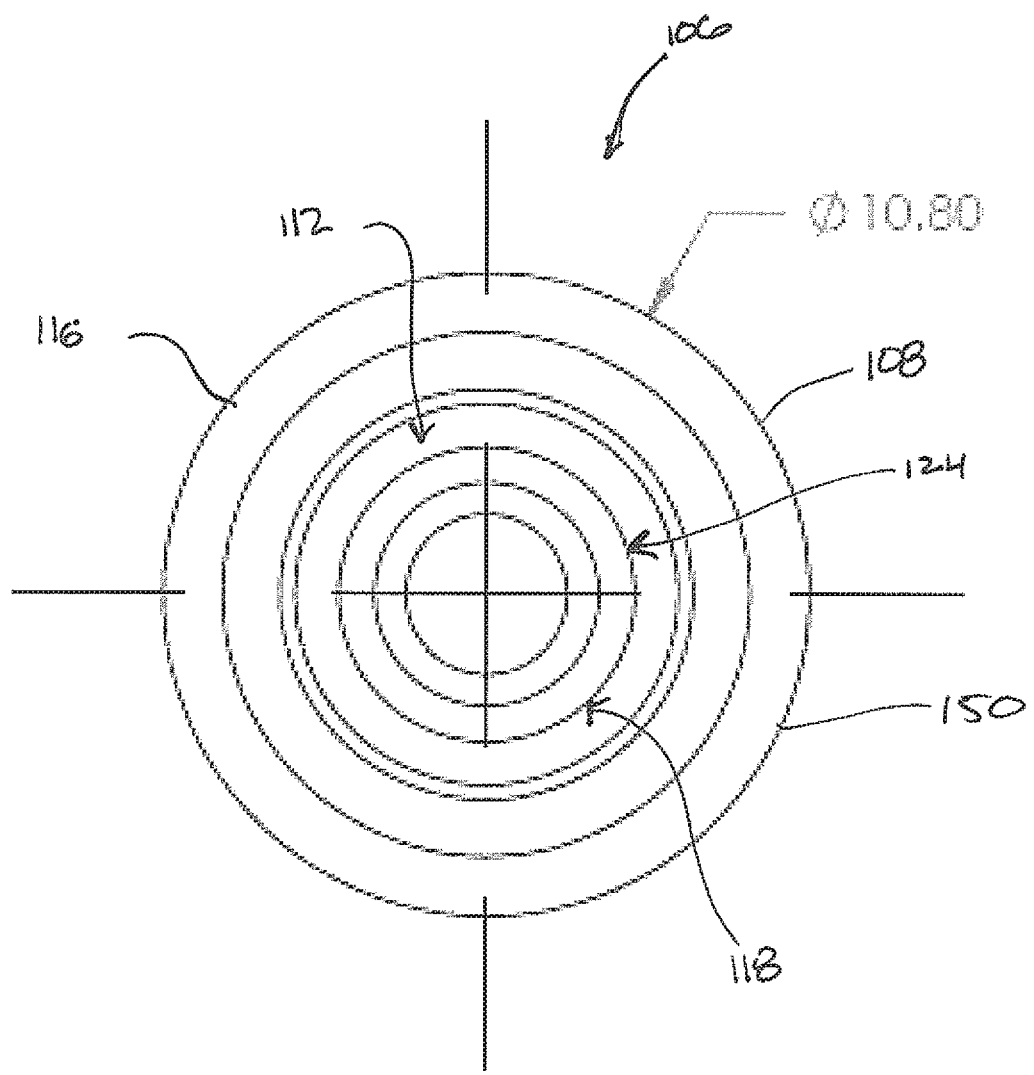
FIG. 4 is top view of the first connecting member of FIG. 1.
Figure 5:
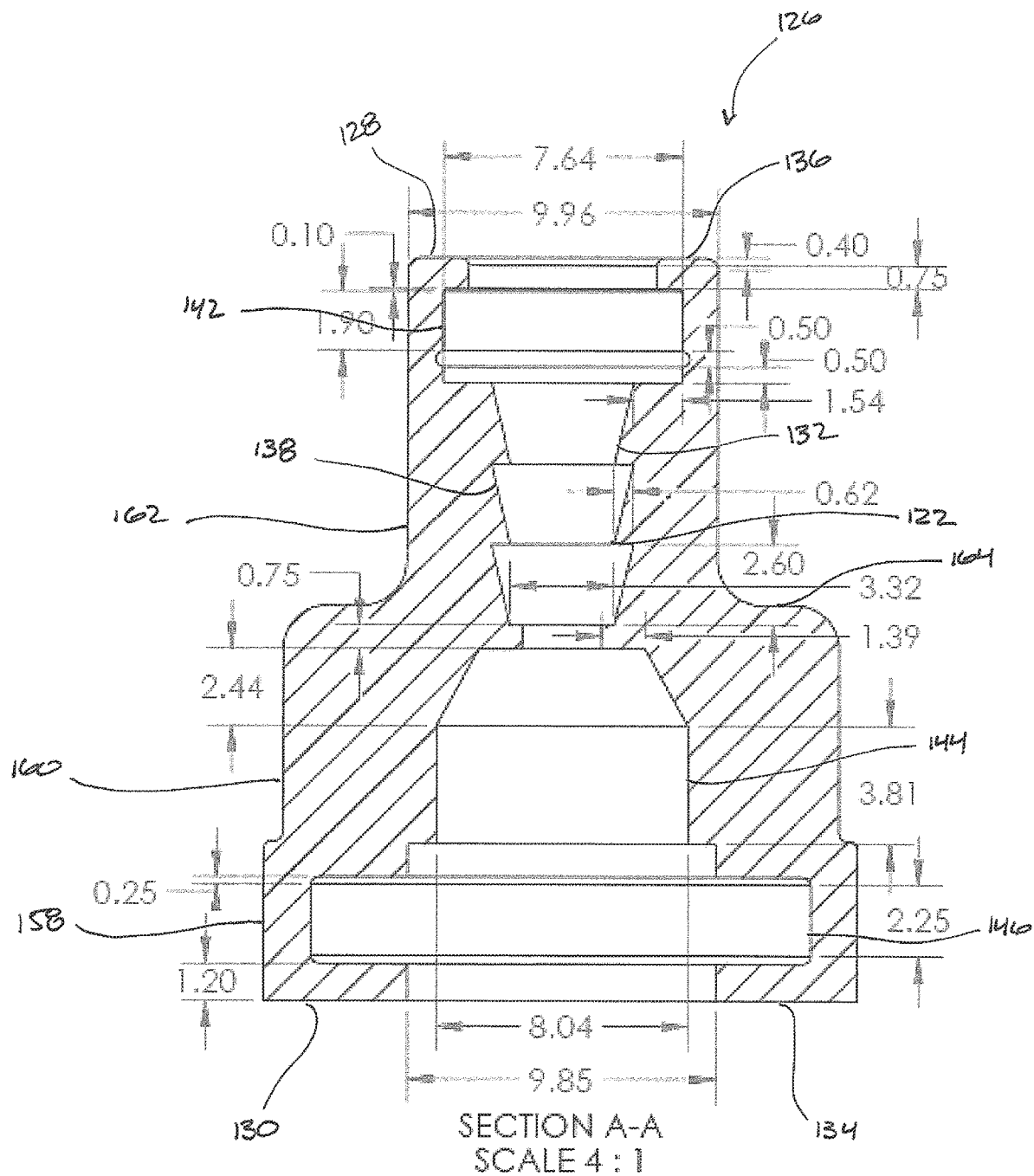
FIG. 5 is a side view partly in section of an embodiment of a second connection of the apparatus.
Figure 6:
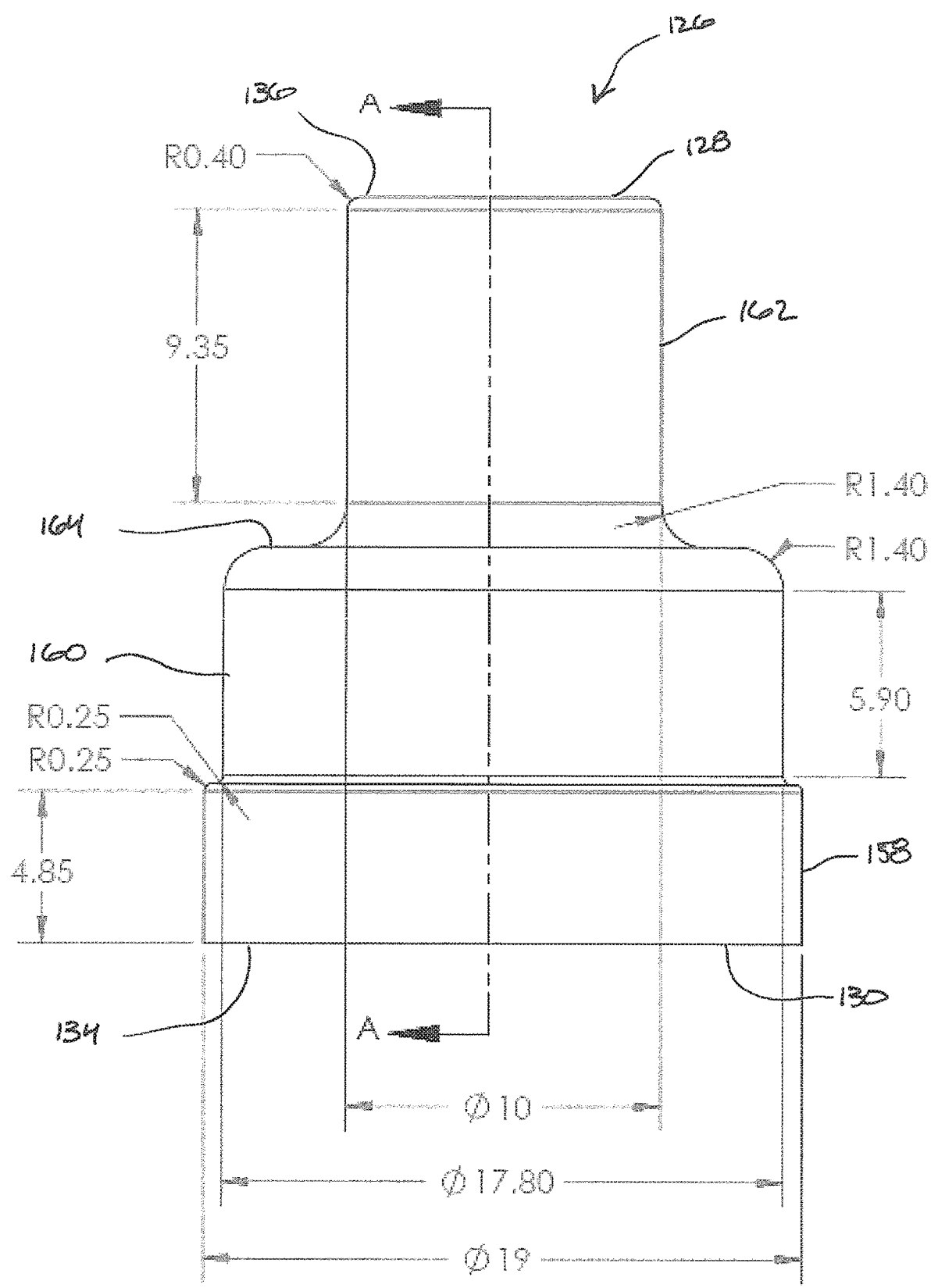
FIG. 6 is a side view of the second connecting member of FIG. 5.
Figure 7:
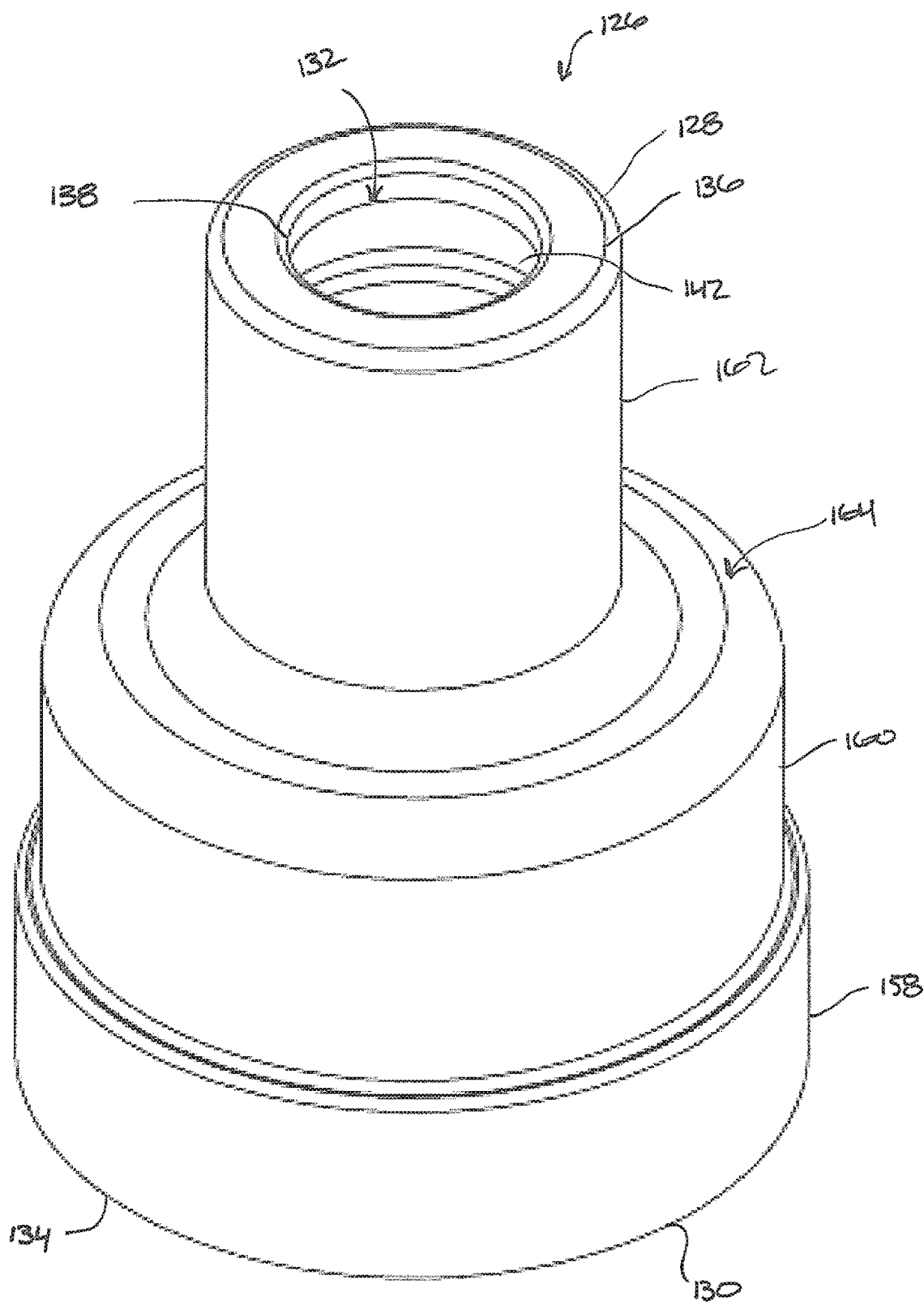
FIG. 7 is an elevated side view of the second connecting member of FIG. 5.
Figure 8:
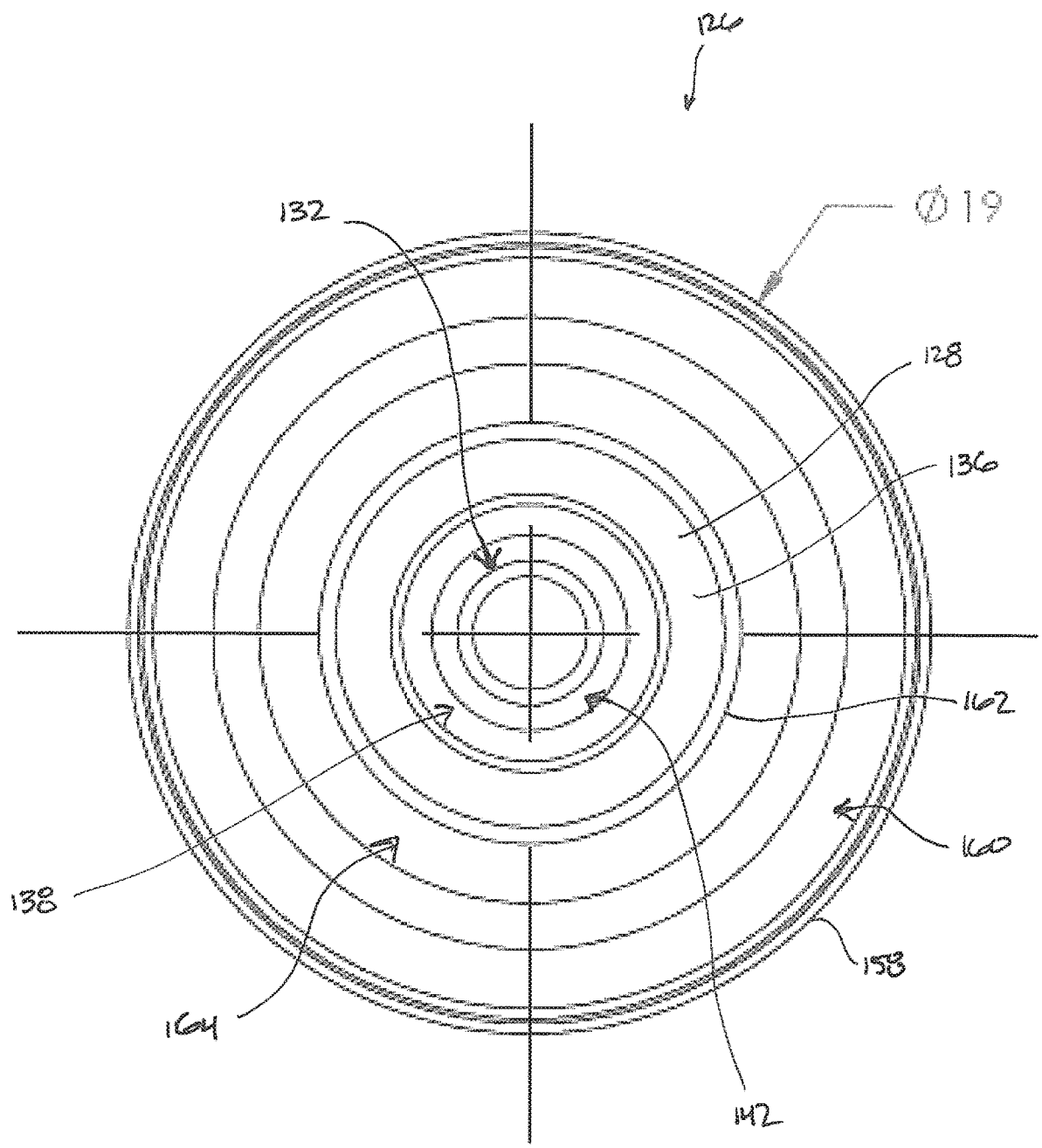
FIG. 8 shows a top view of the second connecting member of FIG. 5.
Figure 9:
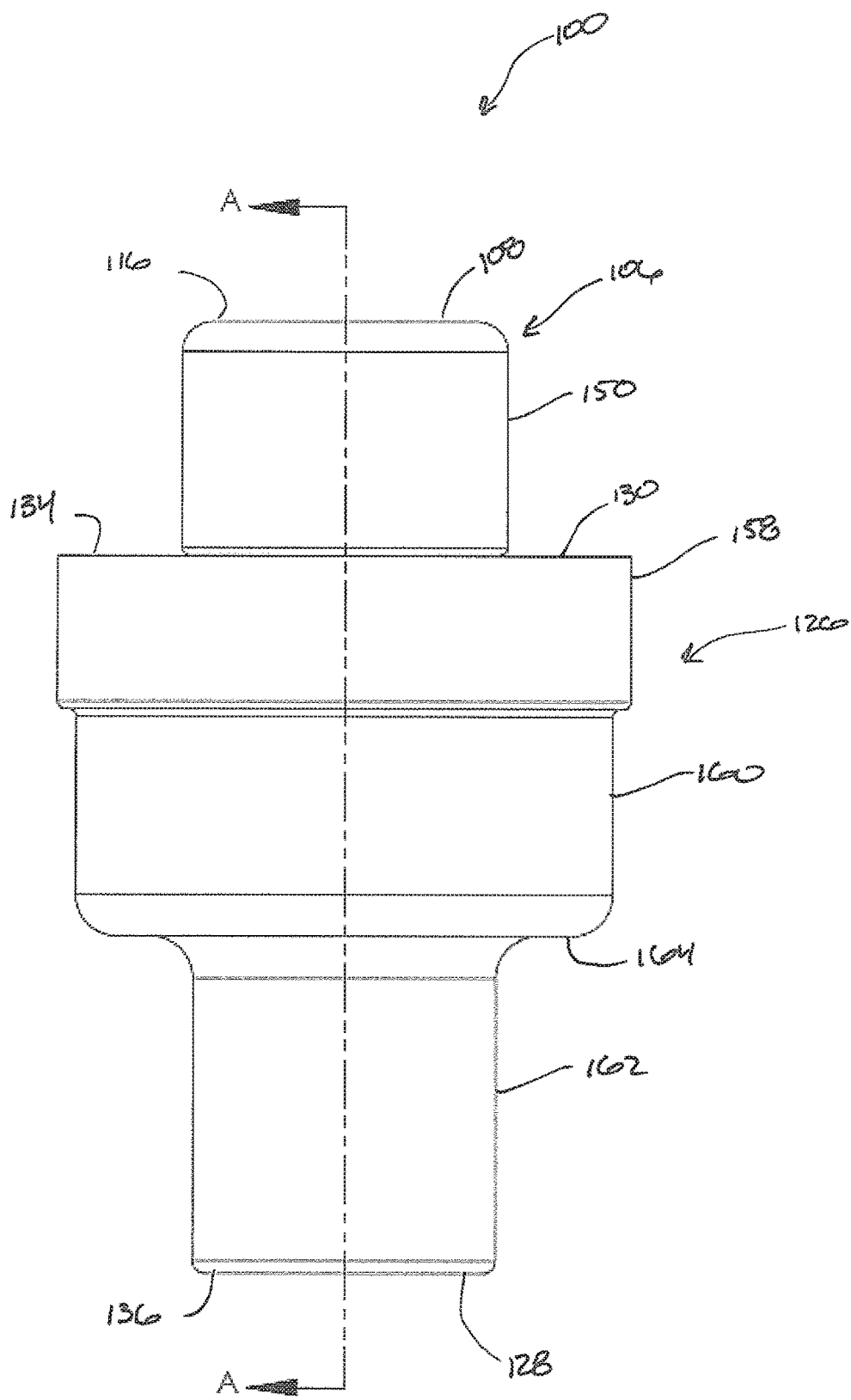
FIG. 9 shows a side view of the first connecting member of FIG. 1 coupled to the second connecting member FIG. 5 in accordance with one embodiment of the invention.
Figure 10:
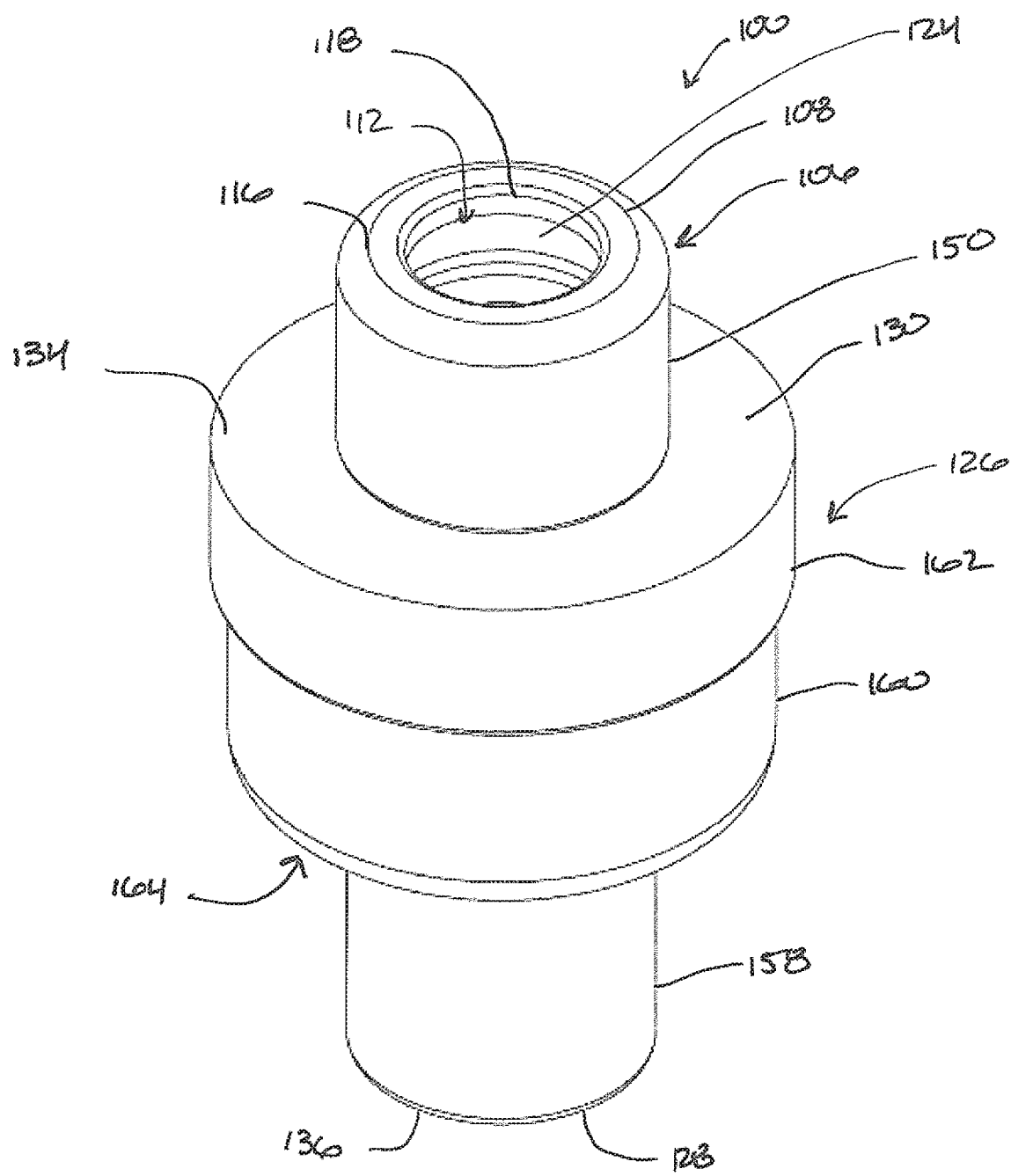
FIG. 10 shows an elevated side view of the first connecting member of FIG. 1 coupled to the second connecting member FIG. 5 in accordance with one embodiment of the invention.
Figure 11:
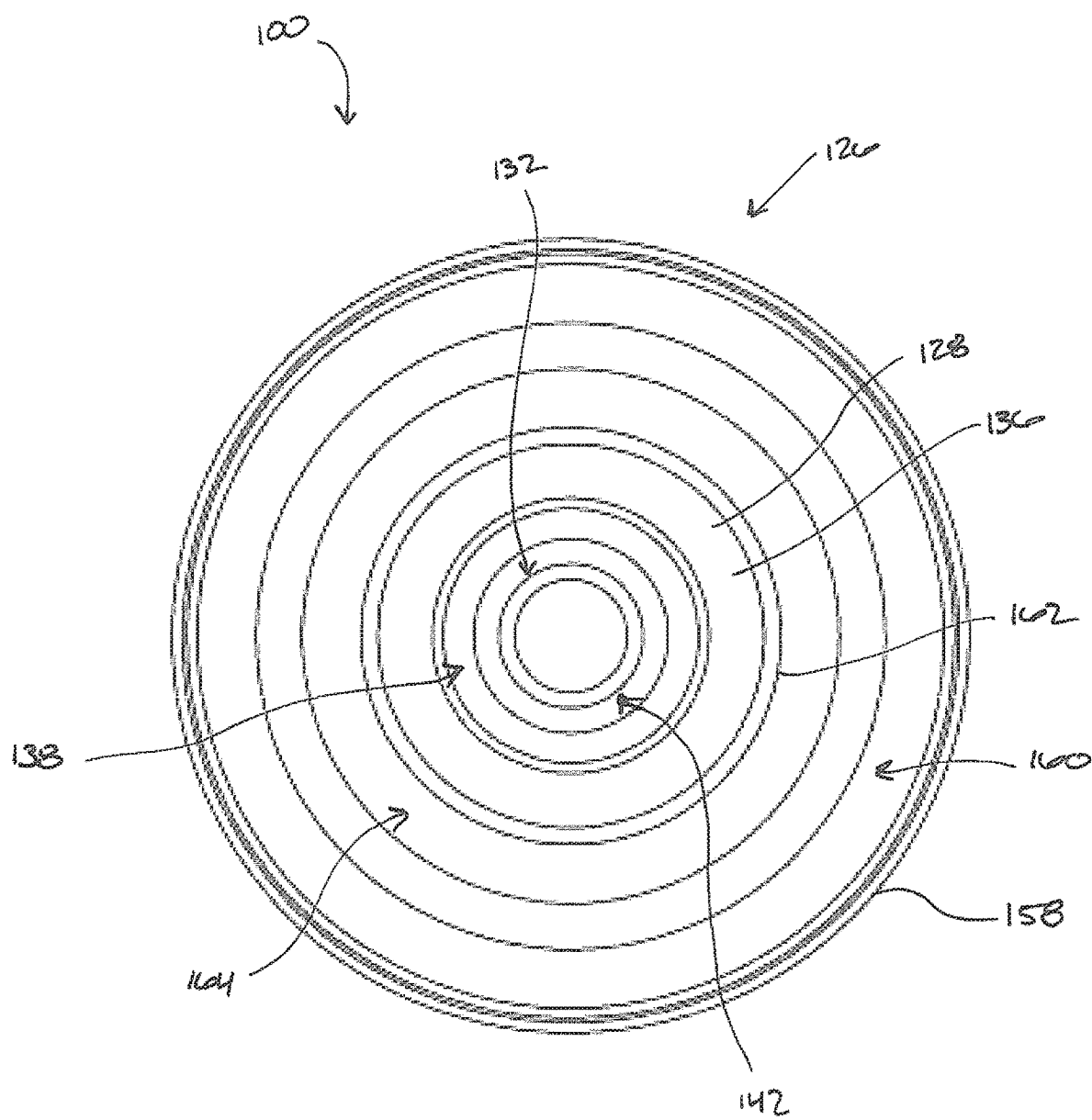
FIG. 11 shows a bottom view of the first connecting member of FIG. 1 coupled to the second connecting member FIG. 5 in accordance with one embodiment of the invention.
Figure 12:
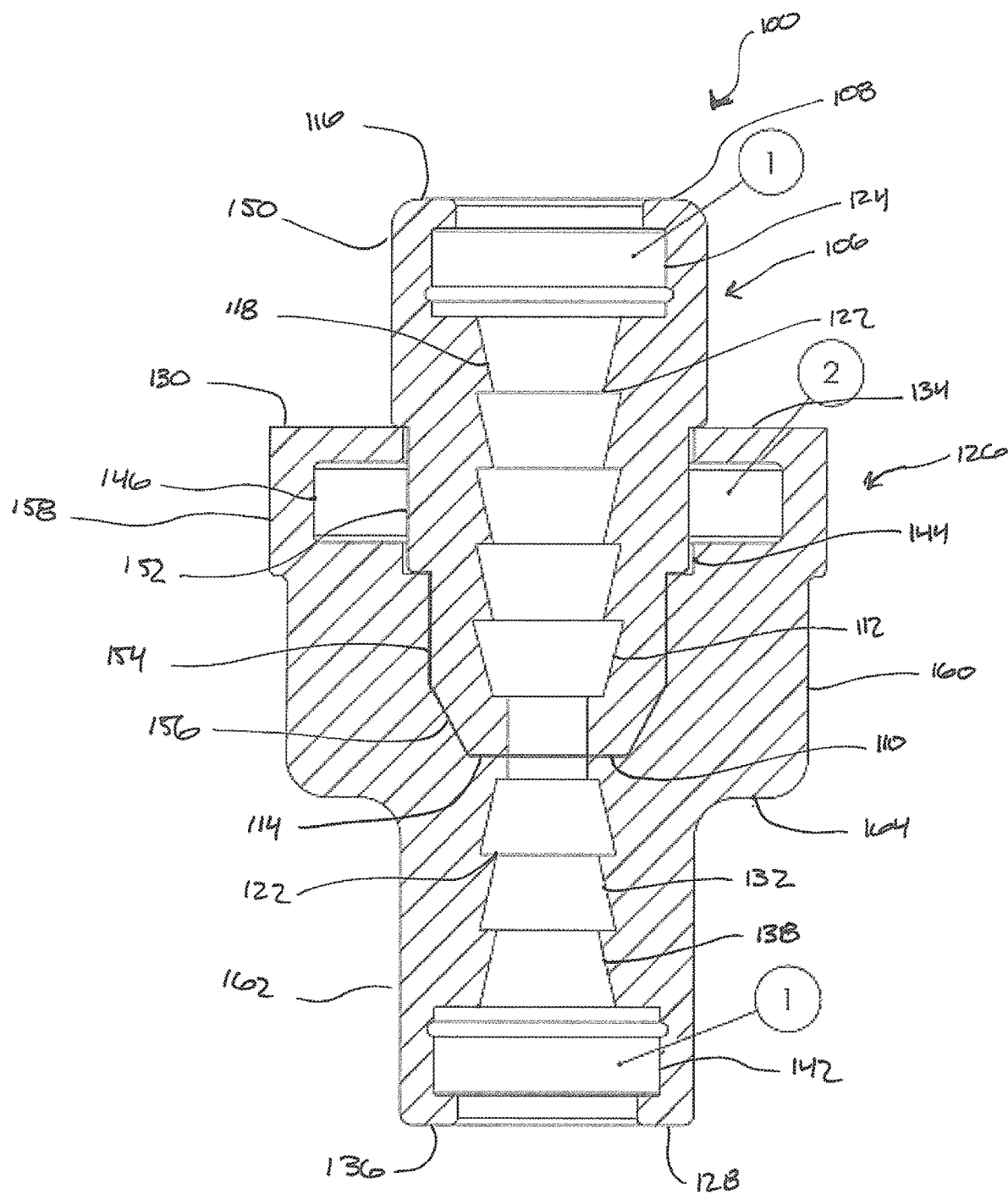
FIG. 12 shows a side view partly in section of the first connecting member of FIG. 1 coupled to the second connecting member FIG. 5 in accordance with one embodiment of the invention.

A nasogastric intubation is the process of inserting a tube through a patients' nasal cavity down to the stomach in order to remove gas and other gastric secretions from the stomach. The tubes can be used to also provide much needed nutrition, water, and medication to the patient. Often the tubes that are inserted into the patient can be accidentally dislodged or forcefully removed by a frightened patient. In such cases re-establishing the tubing can prove to be difficult, endangering the patient. Furthermore, the removal of the in vivo tubing can cause bodily harm to the patient. There is a need for a device that can prevent this forceful removal and allow for quicker re-installation if accidentally disconnected.

The disclosed methods and apparatuses provide for easy installation and removal of a tube during medical procedures. In some embodiments, the disclosed methods and apparatuses may be applied to prevent the accidental removal of the tube in patients undergoing extended treatments involving tubes entering the body in the clinical, geriatric, or other care setting. An additional application allows for the purposeful detachment and sealing of tubes entering the body to allow for increased patient mobility.

The methods and apparatuses disclosed herein are able to connect and disconnect tubes being inserted into a patient's body for fluid or gas flow during any procedure or application requiring medical tubing, including but not limited to: nasogastric intubation, nasotracheal intubation, catheterization, or any application requiring suction. Such devices may prevent accidental removal of the tubes and provide for easy reattachment and reestablishment of fluid or gas flow.

In some applications, the disclosed methods and apparatuses reduce the number of accidental nasogastric (NG) tube pull-outs, therefore reducing the number of times a patient must be re-intubated. This saves money for the hospital (less NG tubes used), time for the nurses, and reduces the chance of trauma to the patient due to subsequent re-intubations (the procedure is very painful and can cause bodily harm). In addition, the detachable design means that patients can get up and walk around between feedings. This will increase the mental and emotional well-being of the patient, who is usually bed-ridden for the duration of the time they are intubated.

FIGS. 9-12 show generally an apparatus 100 for selectively coupling a first tube 102 to a second tube 104. The first tube 102 may be referred to as a distal tube 102. The second tube 104 may be referred to as a proximal tube 104. It should be appreciated that in applications requiring medical tubing, a tube may be disposed inside a patient to perform any medical procedure such as nasogastric intubation, nasotracheal intubation, or catheterization. In some embodiments, the tube may be severed near the tube point of entry into the patient, effectively forming the tube into the first tube 102 and the second tube 104. In other embodiments, separate tubes may be used to perform medical procedures. For example, the second tube 104 may be disposed inside of the patient and a separate first tube 102 may be disposed externally from the patient.

The apparatus 100 may include a first connecting member 106 having a first end 108 adapted to be attached to the first tube 102 and a second end 110 opposite the first end 108. The first connecting member 106 may include the first channel 112 axially extending through the first connecting member 106. In some embodiments, the first connecting member 106 may include a first channel 112 extending through the first connecting member 106 from the first end 108 to the second end 110. The first channel may have a proximal end 114 and a distal end 116.

In some embodiments, a portion of the first channel 112 may be adapted to attachably receive the first tube 102. An interior surface 118 of the first channel 112 may be adapted to attachably receive an exterior surface 120 of the first tube 102 such that fluid communication can exist between the first channel 112 and the first tube 102. For example, the first tube 102 may be attached to the first channel 112 by inserting the first tube 102 into the first channel 112 such that the first tube 102 is retained inside the first channel 112 by friction between the exterior surface 120 of the first tube 102 and the interior surface 118 of the first channel 112.

In some embodiments, the first channel 112 may include at least one anti-withdrawal device 122. The anti-withdrawal device 122 may include ribs, barbs, nodules, or other structures or tube connectors integral with the interior surface 118 of the first channel 112. The anti-withdrawal device 122 may also be separate and non-integral with the interior surface 118 of the first channel 112. The interior surface 118 of the first channel 112 can also be serrated or corrugated in any manner that makes the first tube 102 difficult to remove from the first channel 112 once inserted inside. For example, the interior surface 118 of the first channel 112 may include barbs integral with the interior surface 118, or an inverted and angled tiered press-fit connector.

In other embodiments, the first connecting member 106 may include a first tube connection insert disposed inside of the first channel 112. The first tube connection insert may be adapted to attachably receive the first tube 102. For example, the first tube 102 may be inserted into a channel extending through the first tube connection insert. The first tube connection insert may include the anti-withdrawal device 122. The anti-withdrawal device 122 may or may not be integral with the first tube connection insert. The first tube connection insert may include any rubber, plastic, polymer, or any other suitable material or combination thereof. The first tube connection insert may include the same or dissimilar materials as the first connecting member 106.

The first end 108 of the first connecting member 106 may include a first tube retainer 124 circumferentially disposed within the first channel 112. The first tube retainer 124 may be adapted to create a seal between the first tube 102 and the first channel 112. A sealed connection between the first tube 102 and the first channel 112 may create a leak-proof seal between the first tube 102 and the first connecting member 106. The leak-proof seal may prevent any fluid, including any liquid or gas, from escaping the first channel 112 at the first end 108 of the first connecting member 106. The leak-proof seal may allow the sealed connection between the first tube 102 and the first connecting member 106 to be maintained and to withstand any positive or negative pressure in the first tube 102 or the first channel 112 caused by fluid flowing through the first tube 102 and the first channel 112.

Figure 16:
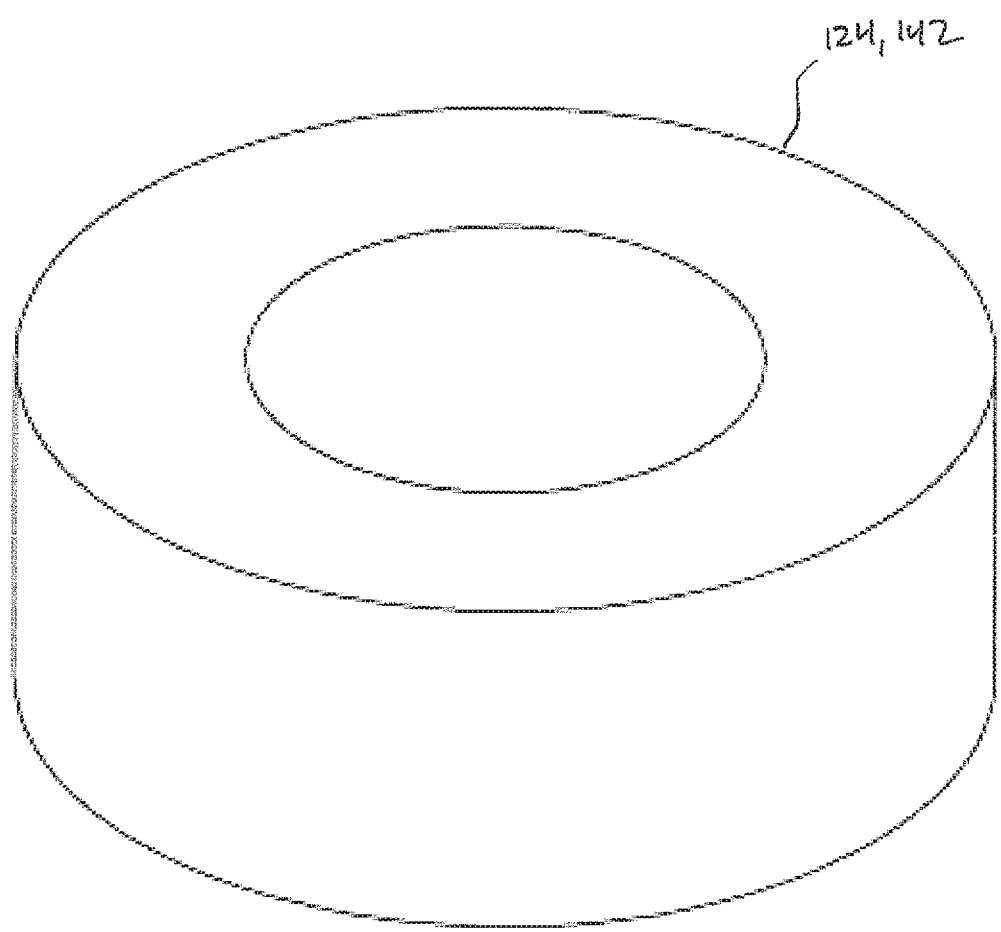
FIG. 16 shows an elevated side view of a tube retainer in accordance with one embodiment of the invention.
Figure 17:
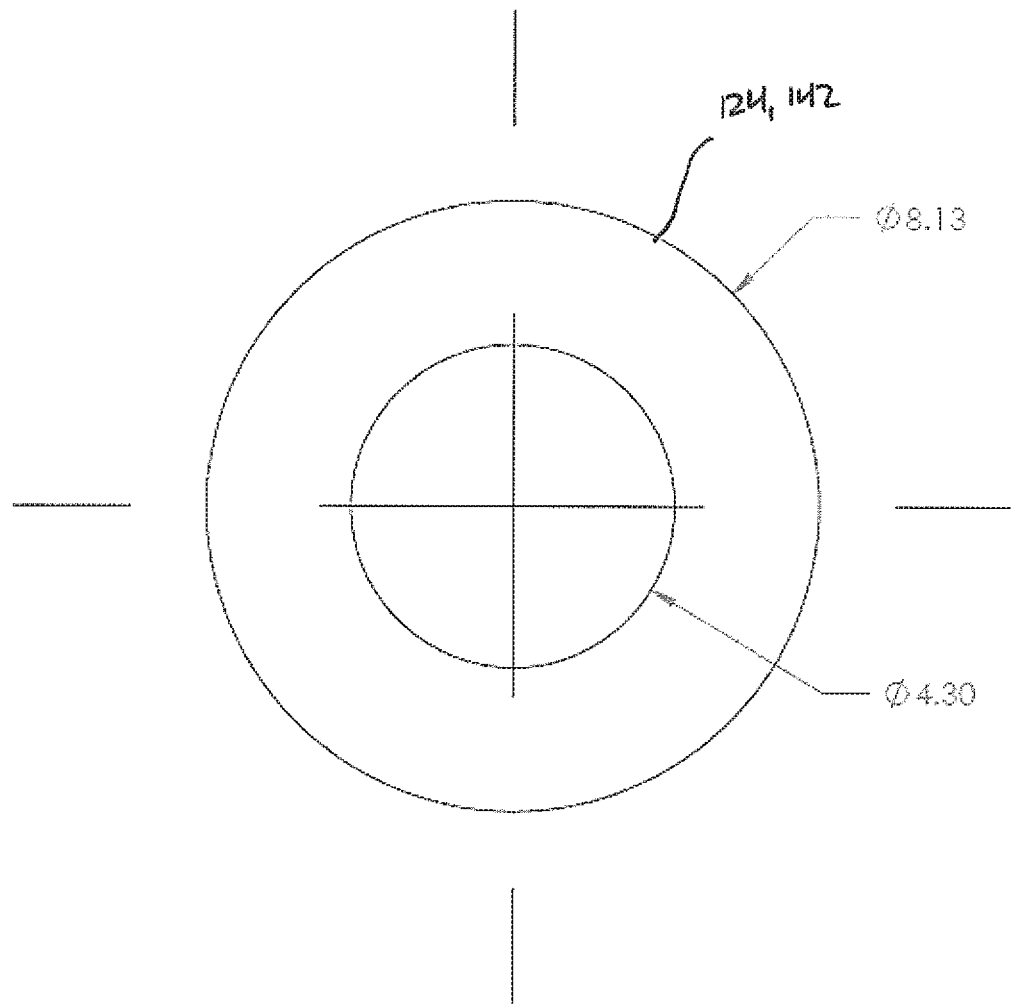
FIG. 17 shows an end view of the tube retainer of FIG. 16.
Figure 18:
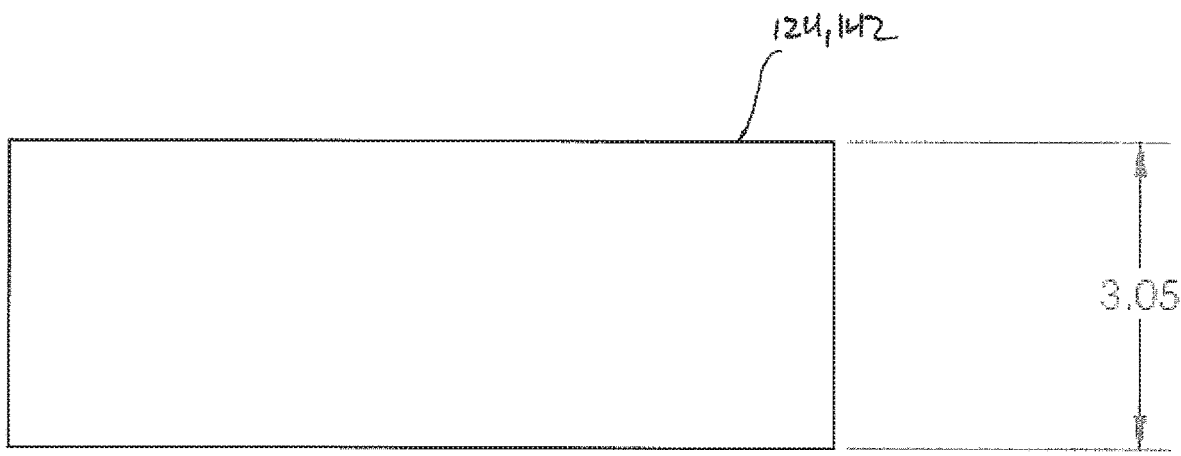
FIG. 18 shows a side view of the tube retainer of FIG. 16.

In some embodiments, the first tube retainer 124 may be an O-ring as shown in FIGS. 16-18. In other embodiments, the first tube retainer 124 may be a fitting, crimp, a change in a diameter of the first channel 112, or other structure suitable for retaining the first tube 102 inside of the first channel 112. In some embodiments, the first tube 102 may be retained inside the first channel 112 by the anti-withdrawal device 122 and the first tube retainer 124. The first tube 102 may be removable from the first channel 112, the anti-withdrawal device 122, and the first tube retainer 124. For example, a medical professional may pull the first tube 102 from the first channel 112 to separate the first tube 102 from the first connecting member 106.

The apparatus 100 may also include a second connecting member 126 selectively couplable to the first connecting member 106. The second connecting member 126 may include a first end 128 adapted to be attached to the second tube 104. The second connecting member 126 may include a second end 130 opposite the first end 128. A second channel 132 may axially extend through the second connecting member 126. In some embodiments, the second channel 132 may extend through the second connecting member 126 from the first end 128 to the second end 130. The second channel 132 may have a proximal end 134 and a distal end 136.

In some embodiments, a portion of the second channel 132 may be adapted to attachably receive the second tube 104. An interior surface 138 of the second channel 132 may be adapted to attachably receive an exterior surface 140 of the second tube 104 such that fluid communication can exist between the second channel 132 and the second tube 104. For example, the second tube 104 may be attached to the second channel 132 by inserting the second tube 104 into the second channel 132 such that the second tube is retained inside the second channel 132 by friction between the exterior surface 140 of the second tube 104 and the interior surface 138 of the second channel 132.

In some embodiments, the second channel 132 may include at least one anti-withdrawal device 122. The anti-withdrawal device 122 may include ribs, barbs, nodules, or other structures or tube connectors integral with the interior surface of the second channel 132. The anti-withdrawal device 122 may also be separate and non-integral with the interior surface 138 of the second channel 132. The interior surface 138 of the second channel 132 can also be serrated or corrugated in any manner that makes the second tube 104 difficult to remove from the second channel 132 once inserted inside. For example, the interior surface 138 of the second channel 132 may include barbs integral with the interior surface 138 or an inverted and angled tiered press-fit connector.

In other embodiments, the second connecting member 126 may include a second tube connection insert disposed inside of the second channel 132. The second tube connection insert may be adapted to attachably receive the second tube 104. For example, the second tube 104 may be inserted into a channel extending through the second tube connection insert. The second tube connection insert may include the anti-withdrawal device 122. The anti-withdrawal device 122 may or may not be integral with the second tube connection insert. The second tube connection insert may include any rubber, plastic, polymer, or any other suitable material or combination thereof. The second tube connection insert may include the same or dissimilar materials as the second connecting member 126.

In some embodiments, the second channel 132 may include an automatic-shutoff valve configured to stop fluid flow through the second tube 104 and the second channel 132 if the first connecting member 106 is decoupled from the second connecting member 126. The apparatus 100 may include a sensor disposed on the first connecting member 106 or the second connecting member 126 configured to detect decoupling of the first connecting member 106 and the second connecting member 126. The sensor may include any type of known sensor, including but not limited to: proximity sensor, infrared sensor, pressure sensor, or magnetic field sensor. In response to detecting that the first connecting member 106 and the second connecting member 126 have been decoupled, the sensor may send a signal to the automatic-shutoff valve to close. In response to receiving the signal from the sensor to close, the automatic-shutoff valve may close and stop fluid flow through the second tube 104 and the second channel 132. The sensor may also be configured to detect recoupling of the first connecting member 106 and the second connecting member 126. In response to detecting that the first connecting member 106 and the second connecting member 126 are recoupled, the sensor may send a signal to the automatic-shutoff valve to open. In response to receiving the signal from the sensor to open, the automatic-shutoff valve may open and reestablish fluid flow through the second tube 104 and the second channel 132. In other embodiments, the first channel 112 may include the automatic shutoff valve. The automatic-shutoff valve may include any type of known valve.

The second end 130 of the second connecting member 126 may include a second tube retainer 142 circumferentially disposed within the second channel 132. The second tube retainer 142 may be adapted to create a seal between the second tube 104 and the second channel 132. A sealed connection between the second tube 104 and the second channel 132 may create a leak-proof seal between the second tube 104 and the second connecting member 126. The leak-proof seal may prevent any fluid, including any liquid or gas, from escaping the second channel 132 at the first end 128 of the second connecting member 126. The leak-proof seal may allow the sealed connection between the second tube 104 and the second connecting member 126 to be maintained and to withstand any positive or negative pressure in the second tube 104 or the second channel 132 caused by fluid flowing through the second tube 104 and the second channel 132.

In some embodiments, the second tube retainer 142 may be an O-ring as shown in FIGS. 16-18. In other embodiments, the second tube retainer 142 may be a fitting, crimp, a change in a diameter of the second channel 132, or other structure suitable for retaining the second tube 104 inside of the second channel 132. In some embodiments, the second tube 104 may be retained inside the second channel 132 by the anti-withdrawal device 122 and the second tube retainer 142. The second tube 104 may be removable from the second channel 132, the anti-withdrawal device 122, and the second tube retainer 142. For example, a medical professional may pull the second tube 104 from the second channel 132 to separate the second tube 104 from the second connecting member 126.

The second end 130 of the second connecting member 126 may include a recess 144 having an interior profile corresponding to an exterior profile of a portion of the first connecting member 106. In some embodiments, the second channel 132 may include the recess 144. In some embodiments, the recess 144 may have an interior profile corresponding to an exterior profile of the second end 110 of the first connecting member 106.

Figure 13:
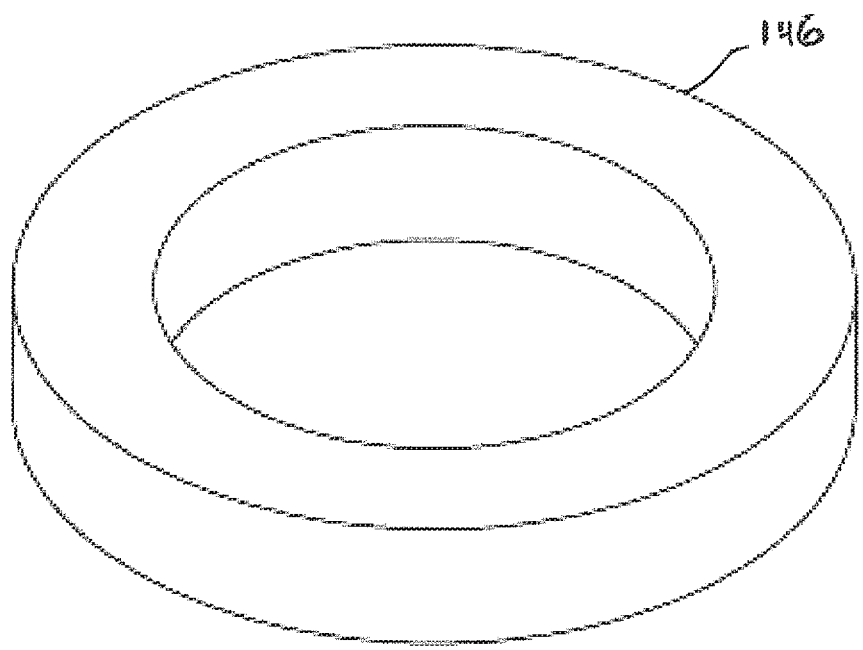
FIG. 13 shows an elevated side view of a retainer in accordance with one embodiment of the invention.
Figure 14:
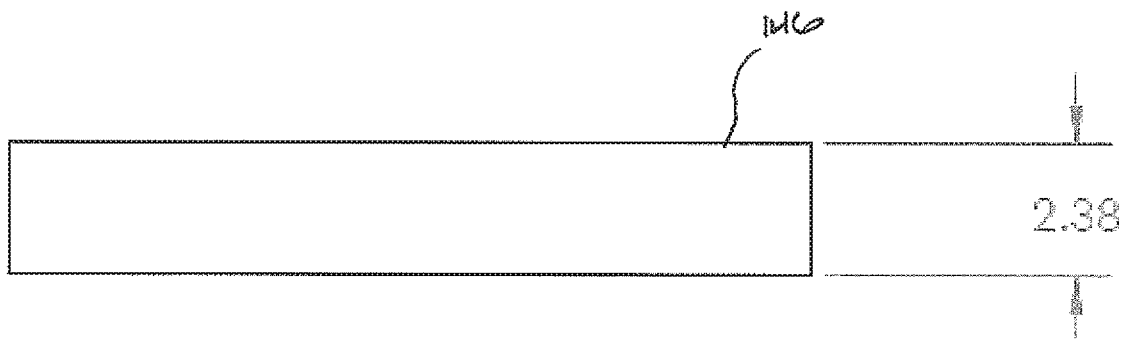
FIG. 14 shows a side view of the retainer of FIG. 13.
Figure 15:
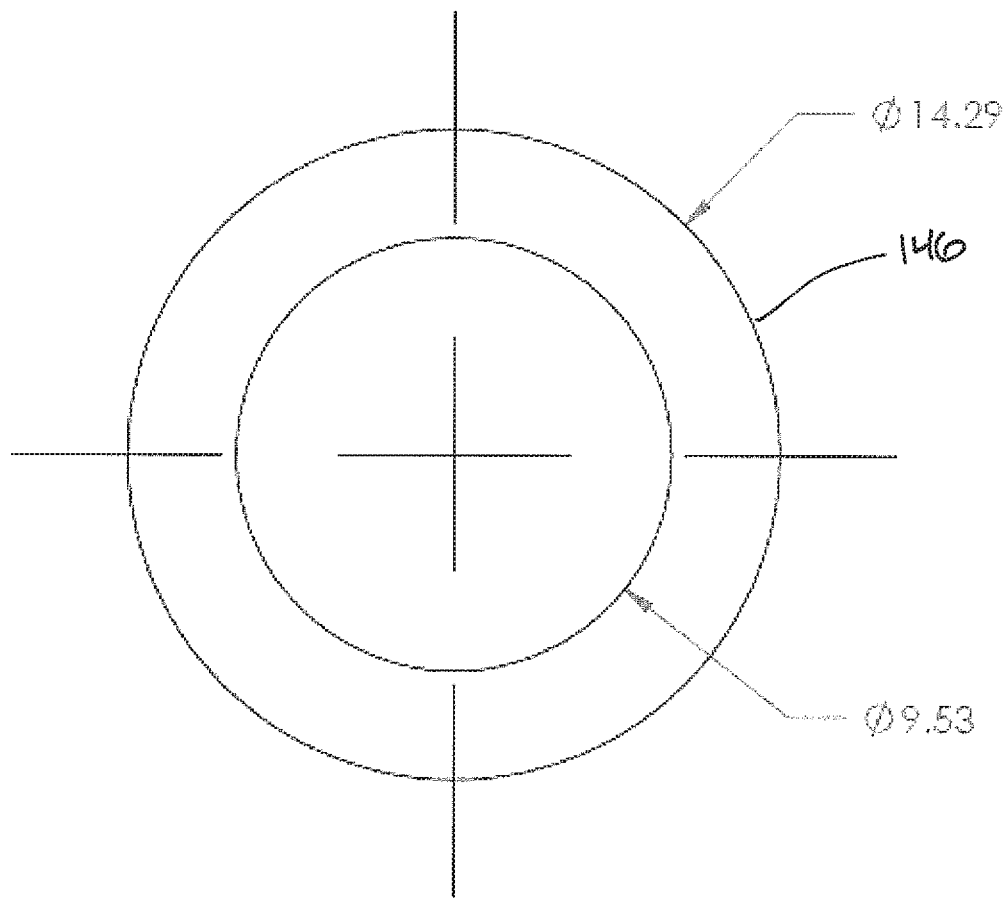
FIG. 15 shows a top view of the retainer of FIG. 13.

At least one of the second end 110 of the first connecting member 106 and the second end 130 of the second connecting member 126 may include a retainer 146. In some embodiments, the retainer 146 may be circumferentially disposed within the recess 144. In some embodiments, the retainer 146 may include an O-ring as shown in FIGS. 13-15. In other embodiments, the retainer 146 may include a fitting, crimp, change in a diameter of the recess 144, or other structure suitable for retaining a portion of the first connecting member 106 inside of the recess 144.

Coupling the second end 130 of the second connecting member 126 to the second end 110 of the first connecting member 106 may cause axial alignment of the first channel 112 and the second channel 132 and may cause the retainer 146 to create a seal between the first connecting member 106 and the second connecting member 126. A sealed connection between the first connecting member 106 and the second connecting member 126 may create a leak-proof seal between the first channel 112 and the second channel 132. The leak-proof seal may create a leak-proof seal between the first tube 102 and the second tube 104. The leak-proof seal may prevent any fluid, including any liquid or gas, from escaping the first channel 112 at the second end 110 of the first connecting member 106. The leak-proof seal may prevent any fluid from escaping the second channel 132 at the second end 130 of the second connecting member 126. The leak-proof seal may prevent any fluid from escaping between the first connecting member 106 and the second connecting member 126. The leak-proof seal may prevent any fluid from escaping the first tube 102 and the second tube 104. The leak-proof seal may allow the sealed connection between the first connecting member 106 and the second connecting member 126 to be maintained and to withstand any positive or negative pressure in the first tube 102, first channel 112, second channel 132, or second tube 104 caused by fluid flow.

Coupling the second end 130 of the second connecting member 126 to the second end 110 of the first connecting member 106 may cause the first channel 112 to be in fluid communication with the second channel 132. In some embodiments, coupling the second connecting member 126 to the first connecting member 106 may cause axial alignment of the proximal end 114 of the first channel 112 and the proximal end 134 of the second channel 132. Coupling the second connecting member 126 and the first connecting member 106 may cause the exterior profile of the portion of the first connecting member 106 to engage the interior profile of the recess 144 of the second connecting member 126. In some embodiments, coupling the second connecting member 126 and the first connecting member 106 may cause the exterior profile of the second end 110 of the first connecting member 106 to engage the interior profile of the recess 144 of the second end 130 of the second connecting member 126.

Figure 20:
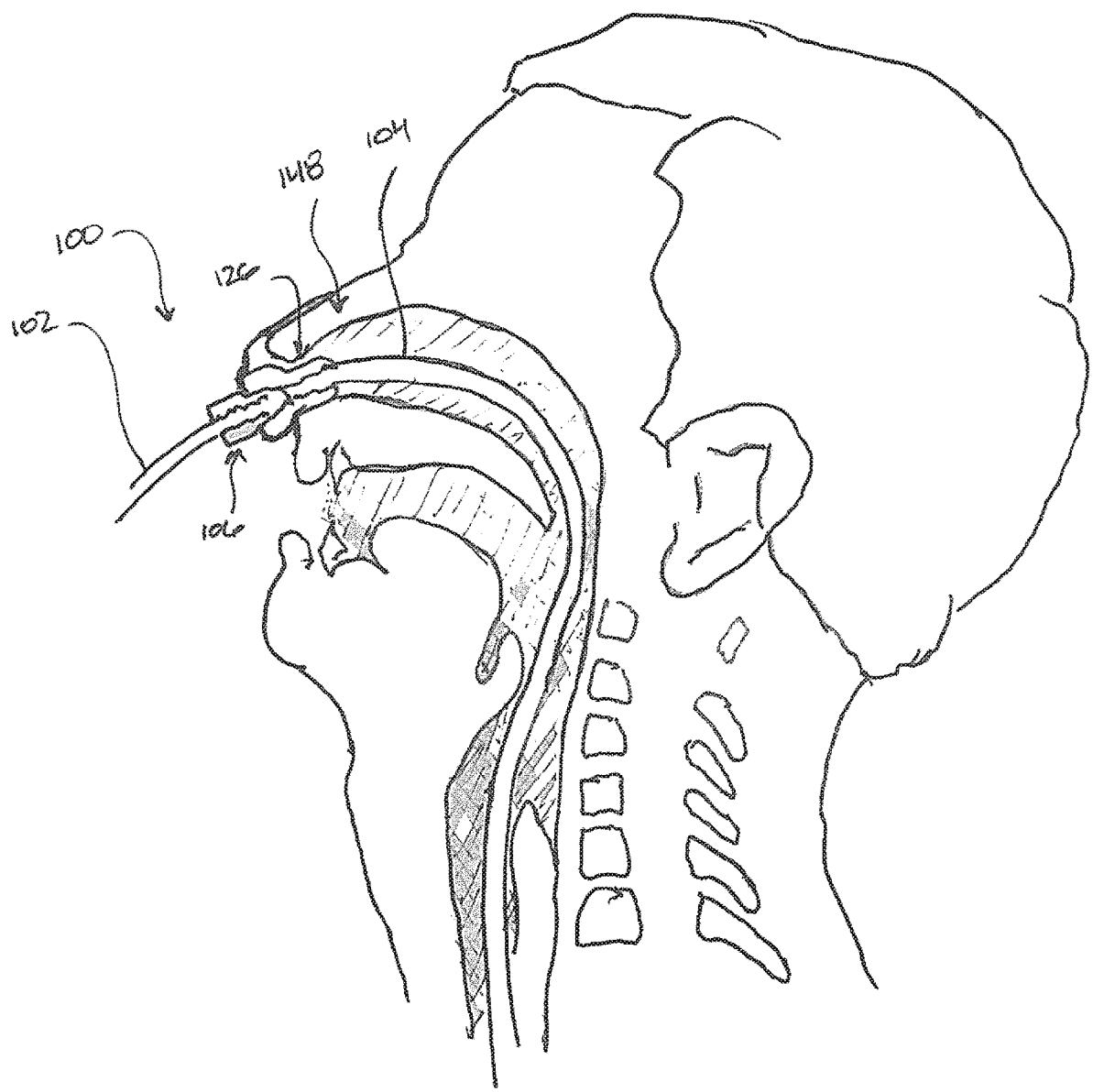
FIG. 20 shows a cross-sectional view of the apparatus inserted into the nostril of a patient during nasogastric intubation.
Figure 21:
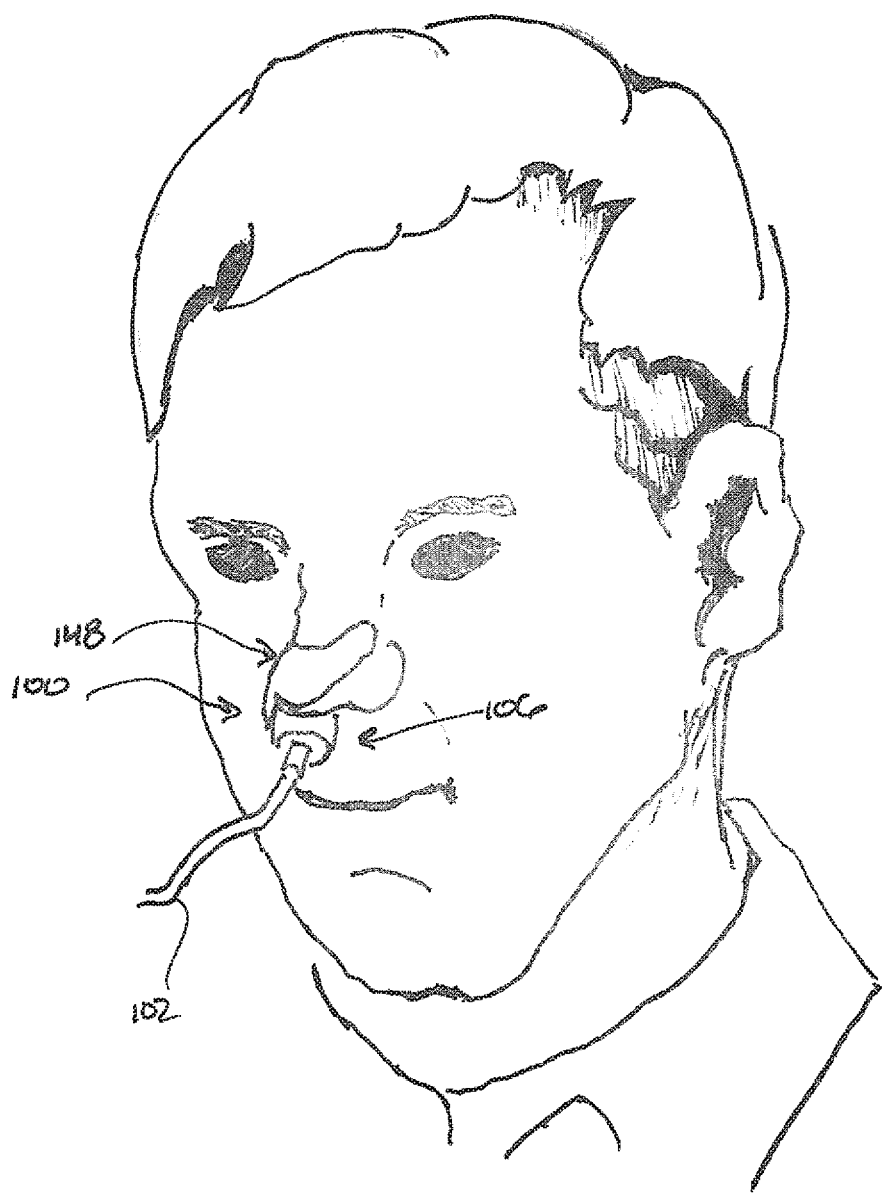
FIG. 21 shows a front view of the patient of FIG. 20 during nasogastric intubation using the apparatus according to one embodiment.

In some embodiments, the apparatus 100 shown in FIGS. 9-12 may be applied to a medical procedure requiring tubing, such as a nasogastric intubation procedure. In such embodiments, the first tube 102 may be disposed externally from a patient nostril 148 and a portion of the second tube 104 may be disposed internally to the patient nostril 148 as shown in FIGS. 20-21. In other embodiments, the portion of the second tube 104 may be disposed internally to any portion of the patient. At least one of the first end 108 of the first connecting member 106 and the first end 128 of the second connecting member 126 may be adapted to be inserted into the patient nostril 148. In some embodiments, the first end 128 of the second connecting member 126 may be adapted to be inserted into the patient nostril 148.

In some embodiments, the first connecting member 106 and the second connecting member 126 may include a malleable material. Including the malleable material may allow the first connecting member 106 and the second connecting member 126 to comfortably engage the nostril or any other portion of the patient. The first connecting member 106 and the second connecting member 126 may include any material that is easily sterilized for use in medical applications and may include any material that is biologically inert to safely contact any portion of the patient. The first connecting member 106 and the second connecting member 126 may include any rubber, plastic, polymeric, or any other suitable material or combination thereof. In some embodiments, the first connecting member 106 and the second connecting member 126 may include polymeric materials including, but not limited to: silicone rubber, natural rubber, PVC, polyurethane, nylon, polyester, polysulfones, hydrogels, polyphosphazenes, or thermoplastic elastomers. The first connecting member 106 and the second connecting member 126 may include identical or dissimilar materials.

The first tube 102 and second tube 104 may include any rubber, plastic, polymeric, or any other suitable material or combination thereof. The first tube 102 and second tube 104 may include any tubing type used for any medical procedure, including but not limited to: lumen nasogastric tubing, percutaneous endoscopic gastrostomy (PEG) tubing, jejunostomy tubing (J-tubes), Dobhoff tubing, naso-duodenal (ND) tubing, and naso-jejunal (NJ) tubing. Any fluid may flow through the first tube 102, first channel 112, second tube 104, and second channel 132, including but not limited to: air, water, liquid feeding formula, gastric secretions, chyme, or any other liquid or gas.

FIGS. 1-4 show generally the first connecting member 106 of the apparatus 100. In some embodiments, the first connecting member 106 may include a first portion 150 extending from the first end 108 of the first connecting member 106 to a second portion 152. The first portion 150 may include a generally cylindrical profile having a first diameter. The first connecting member 106 may include the second portion 152 extending from the first portion 150 to a third portion 154. The second portion 152 may include a generally cylindrical profile having a second diameter that is smaller than the first diameter. The first connecting member 106 may include the third portion 154 extending from the second portion 152 to the second end 110 of the first connecting member 106. The third portion 154 may include a generally cylindrical profile having a third diameter that is smaller than the second diameter. The second end 110 of the first connecting member 106 may include a beveled edge 156. The second portion 152 and the third portion 154 may define the exterior profile of the second end 110 of the first connecting member 106 corresponding to the interior profile of the recess 144. The first portion 150, the second portion 152, and the third portion 154 may include any profile and may be of any length, width, height, or diameter. The first connecting member 106 may include more or less portions than the first portion 150, the second portion 152, and third portion 154, and may include an exterior profile having any prismatic or amorphous shape.

FIGS. 5-8 show generally the second connecting member 126 of the apparatus 100. In some embodiments, the second connecting member 126 may include a first portion 158 that extends from the second end 130 of the second connecting member 126 to a second portion 160. The first portion 158 may include a generally cylindrical profile having a first diameter. The second connecting member 126 may include the second portion 160 that extends from the first portion 158 to a third portion 162. The second portion 160 may include a generally cylindrical profile having a second diameter that is smaller than the first diameter. The second connecting member 126 may include the third portion 162 that extends from the second portion 160 to the first end 128 of the second connecting member 126. The third portion 162 may include a generally cylindrical profile and may include a third diameter that is smaller than the second diameter. The first portion 158, the second portion 160, and third portion 162 may include any profile and may be of any length, width, height, or diameter. The second connecting member 126 may include more or less portions than the first portion 158, the second portion 160, and third portion 162, and may include an exterior profile having any prismatic or amorphous shape.

In some embodiments, an interior profile of the first portion 158 and an interior profile of the second portion 160 may define the recess 144. The first portion 150 may include the retainer 146. In other embodiments, any portion of the second connecting member 126 may include the retainer 146. The retainer 146 may be disposed circumferentially anywhere within the recess 144. An exterior profile of the second portion 160 and an exterior profile of the third portion 162 may define a shoulder 164 between the second portion 160 and the third portion 162. In some embodiments, the shoulder 164 may be located anywhere on the exterior profile of the second connecting member 126. The shoulder 164 may also extend radially from the second connecting member 126 by any distance.

Figure 19:
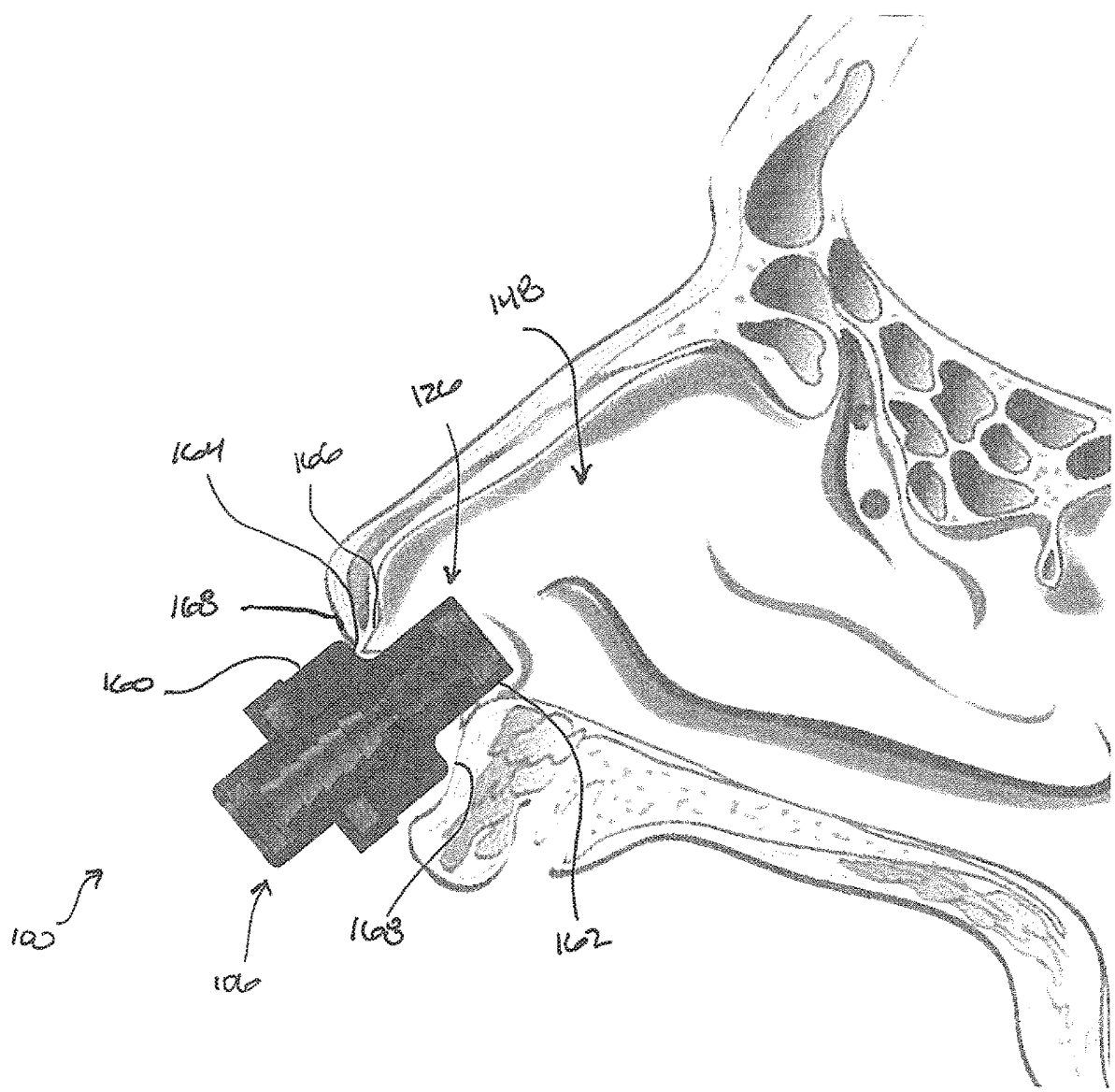
FIG. 19 shows a cross-sectional view of the apparatus inserted into the nasal vestibule of a patient in accordance with one embodiment of the invention.

As shown in FIG. 19, in some embodiments, the third portion 162 may be adapted to engage a nasal vestibule 166 of the patient and the shoulder 164 may be adapted to prevent the second portion 160 from passing beyond an epithelium lining 168 of the nasal vestibule 166.

A method for selectively coupling the first tube 102 to the second tube 104 may include attaching the first tube 102 to the first channel 112 of the first connecting member 106, where the first channel 112 extends axially through the first connecting member 106. The method may include attaching the second tube 104 to the second channel 132 of the second connecting member 126, where the second channel 132 extends axially through the second connecting member 126. The method may include coupling the first connecting member 106 to the second connecting member 126 by inserting the portion of the first connecting member 106 inside the recess 144 of the second connecting member 126 such that the first channel 112 and the second channel 132 are axially aligned, where the recess 144 has an interior profile corresponding to an exterior profile of the portion of the first connecting member 106.

In some embodiments, the method may include intubating the patient through the nose using a tube.

In some embodiments, the method may include severing a tube into the first tube 102 and the second tube 104. The first tube 102 may be disposed externally from the patient and the portion of the second tube 104 may be disposed internally to the patient as shown in FIGS. 20-21.

In some embodiments, the method may include coupling the portion of the second connecting member 126 to the patient.

In some embodiments, the method may include decoupling the first connecting member 106 from the second connecting member 126 by removing the portion of the first connecting member 106 from the recess 144 of the second connecting member 126.

In one example, the apparatus 100 may be used as follows: The patient may be intubated using a tube. The tube may be severed near the tube point of entry into the patient into the first tube 102 and the second tube 104. The first tube 102 may be disposed externally from the patient and the portion of the second tube 104 may be disposed internally to the patient. A severed end of the second tube 104 may be inserted into the second channel 132 at the first end 128 of the second connecting member 126. The second tube 104 may extend through the second tube retainer 142 to create a sealed connection between the second tube 104 and the second channel 132. The second tube 104 may be retained inside the second channel 132 by the anti-withdrawal device 122 and the second tube retainer 142. As shown in FIG. 19, the third portion 154 of the second connecting member 126 may be inserted into the patient nasal vestibule 166, where the shoulder 164 may engage the epithelium lining 168 of the nasal vestibule 166 to prevent the second connecting member 126 from being further inserted into a nasal cavity of the patient.

The severed end of the first tube 102 may be inserted into the first channel 112 at the first end 108 of the first connecting member 106. The first tube 102 may extend through the first tube retainer 124 to create a sealed connection between the first tube 102 and the first channel 112. The first tube 102 may be retained inside the first channel 112 by the anti-withdrawal device 122 and the first tube retainer 124.

The second end 110 of the first connecting member 106 may be coupled to the second end 130 of the second connecting member 126 by engaging the recess 144 of the second connecting member 126 with the second end 110 of the first connecting member 106. The second end 110 of the first connecting member 106 may extend through the retainer 146 to create a sealed connection between the first connecting member 106 and the second connecting member 126. Coupling the first connecting member 106 to the second connecting member 126 may cause the first tube 102 and the second tube 104 to be in fluid communication. Coupling the first connecting member 106 to the second connecting member 126 may also cause the first channel 112 and the second channel 132 to be in fluid communication. While the first connecting member 106 and the second connecting member 126 are coupled, fluid may be delivered to the patient through the first tube 102, the first channel 112, the second tube 104, and the second channel 132.

The first connecting member 106 may be decoupled from the second connecting member by removing the second end 110 of the first connecting member 106 from the recess 144 of the second connecting member 126. Decoupling the first connecting member 106 from the second connecting member 126 may break fluid communication between the first tube 102 and the second tube 104. Decoupling the first connecting member 106 from the second connecting member 126 may also break fluid communication between the first channel 112 and the second channel 132. The first connecting member 106 and the second connecting member 126 may be decoupled accidentally or purposefully by the patient or the medical professional such that the first tube 102 and second tube 104 may disconnect while the portion of the second tube 104 remains disposed internal to the patient.

Once the first connecting member 106 is decoupled from the second connecting member 126, the first connecting member 106 and the second connecting member 126 may be recoupled using the above described processes according to the needs of the patient or the medical professional.

The first tube 102 may be pulled from the first channel 112, the first tube retainer 124, and the anti-withdrawal device 122 to separate the first tube 102 from the first connecting member 106.

The second tube 104 may be pulled from the second channel 132, the second tube retainer 142, and the anti-withdrawal device 122 to separate the second tube 104 from the second connecting member 126.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An apparatus for selectively coupling a first tube to a second tube, comprising:
   a first connecting member including:
      a first end adapted to be attached to the first tube;
      a second end opposite the first end; and
      a first channel extending through the first connecting member from the first end to the second end; and
   a second connecting member selectively couplable to the first connecting member, the second connecting member including:
      a first end adapted to be attached to the second tube;
      a second end opposite the first end; and
      a second channel extending through the second connecting member from the first end to the second end,
   wherein at least one of the second end of the first connecting member and the second end of the second connecting member includes a retainer, wherein the second end of the second connecting member includes a recess having an interior profile corresponding to an exterior profile of the second end of the first connecting member, wherein coupling the second end of the second connecting member to the second end of the first connecting member causes axial alignment of the first channel and the second channel and causes the retainer to create a seal between the first connecting member and the second connecting member, wherein at least one of the first end of the first connecting member and the first end of the second connecting member is adapted to be inserted into a nostril of a patient; and wherein the second connecting member comprises:
a first portion that extends from the second end of the second connecting member to a second portion, wherein the first portion includes a generally cylindrical profile having a first diameter;
the second portion that extends from the first portion to a third portion, wherein the second portion includes a generally cylindrical profile having a second diameter that is smaller than the first diameter, and
the third portion that extends from the second portion to the first end of the second connecting member, wherein the third portion includes a generally cylindrical profile and includes a third diameter that is smaller than the second diameter;

wherein an interior profile of the first portion and an interior profile of the second portion define the recess,
wherein the first portion includes the retainer;
wherein an exterior profile of the second portion and an exterior profile of the third portion define a shoulder between the second portion and the third portion; and
wherein the third portion is adapted to engage a nasal vestibule of the patient and the shoulder is adapted to prevent the second portion from passing beyond an epithelium lining of the nasal vestibule.

2. The apparatus of claim 1, wherein the first tube is adapted to be disposed externally from the patient nostril and a portion of the second tube is adapted to be disposed internally to the nostril of the patient.

3. The apparatus of claim 1, wherein a portion of the first channel is adapted to attachably receive the first tube and a portion of the second channel is adapted to attachably receive the second tube.

4. The apparatus of claim 3, wherein the first channel includes at least one anti-withdrawal device and the second channel includes the recess and at least one anti-withdrawal device.

5. The apparatus of claim 1, wherein:
the first end of the first connecting member includes a first tube retainer circumferentially disposed within the first channel and the first end of the second connecting member includes a second tube retainer circumferentially disposed within the second channel,
the first tube retainer being adapted to create a seal between the first tube and the first channel, and
the second tube retainer being adapted to create a seal between the second tube and the second channel.

6. The apparatus of claim 5, wherein the retainer, the first tube retainer, and the second tube retainer are O-rings.

7. The apparatus of claim 1, wherein the retainer is circumferentially disposed within the recess.

8. The apparatus of claim 1, wherein the first end of the second connecting member is adapted to be inserted into the nostril of the patient.

9. The apparatus of claim 1, wherein the first connecting member and second connecting member include a malleable material.

10. An apparatus for selectively coupling a first tube to a second tube, comprising:
a first connecting member including:
a first end adapted to be attached to the first tube;
a second end opposite the first end; and
a first channel extending through the first connecting member from the first end to the second end; and
a second connecting member selectively couplable to the first connecting member, the second connecting member including:
a first end adapted to be attached to the second tube;
a second end opposite the first end; and
a second channel extending through the second connecting member from the first end to the second end,
wherein at least one of the second end of the first connecting member and the second end of the second connecting member includes a retainer,
wherein the second end of the second connecting member includes a recess having an interior profile corresponding to an exterior profile of the second end of the first connecting member,
wherein coupling the second end of the second connecting member to the second end of the first connecting member causes axial alignment of the first channel and the second channel and causes the retainer to create a seal between the first connecting member and the second connecting member,
wherein at least one of the first end of the first connecting member and the first end of the second connecting member is adapted to be inserted into a nostril of a patient,
wherein the first connecting member comprises:
a first portion extending from the first end of the first connecting member to a second portion, wherein the first portion includes a generally cylindrical profile having a first diameter;
the second portion extending from the first portion to a third portion, wherein the second portion includes a generally cylindrical profile having a second diameter that is smaller than the first diameter; and
the third portion extending from the second portion to the second end of the first connecting member, wherein the third portion includes a generally cylindrical profile having a third diameter that is smaller than the second diameter,
wherein the second end of the first connecting member includes a beveled edge, and
wherein the second portion and the third portion define the exterior profile of the second end of the first connecting member corresponding to the interior profile of the recess.

11. The apparatus of claim 10, wherein the first tube is adapted to be disposed externally from the patient nostril and a portion of the second tube is adapted to be disposed internally to the nostril of the patient.

12. The apparatus of claim 10, wherein a portion of the first channel is adapted to attachably receive the first tube and a portion of the second channel is adapted to attachably receive the second tube.

13. The apparatus of claim 12, wherein the first channel includes at least one anti-withdrawal device and the second channel includes the recess and at least one anti-withdrawal device.

14. The apparatus of claim 10, wherein:
the first end of the first connecting member includes a first tube retainer circumferentially disposed within the first channel and the first end of the second connecting member includes a second tube retainer circumferentially disposed within the second channel,
the first tube retainer being adapted to create a seal between the first tube and the first channel, and
the second tube retainer being adapted to create a seal between the second tube and the second channel.

15. The apparatus of claim 10, wherein the retainer is circumferentially disposed within the recess and wherein the first end of the second connecting member is adapted to be inserted into the nostril of the patient.

16. The apparatus of claim 10, wherein the first connecting member and second connecting member include a malleable material.

17. An apparatus for selectively coupling a first tube to a second tube, comprising:
a first connecting member including a first channel axially extending through the first connecting member, the first channel having a proximal end and a distal end,
wherein a portion of the first channel is adapted to attachably receive the first tube; and
a second connecting member selectively couplable to the first connecting member,
wherein a second channel axially extends through the second connecting member, the second channel having a proximal end of the second channel and a distal end of the second channel,
wherein a portion of the second channel is adapted to attachably receive the second tube,
wherein the second connecting member includes a recess having an interior profile corresponding to an exterior profile of a portion of the first connecting member, and
wherein coupling the second connecting member to the first connecting member causes axial alignment of the proximal end of first channel and the proximal end of the second channel;

wherein the first connecting member comprises:
a first portion extending from the first end of the first connecting member to a second portion, wherein the first portion includes a generally cylindrical profile having a first diameter;
the second portion extending from the first portion to a third portion, wherein the second portion includes a generally cylindrical profile having a second diameter that is smaller than the first diameter; and
the third portion extending from the second portion to the second end of the first connecting member, wherein the third portion includes a generally cylindrical profile having a third diameter that is smaller than the second diameter,
wherein the second end of the first connecting member includes a beveled edge, and
wherein the second portion and the third portion define the exterior profile of the second end of the first connecting member corresponding to the interior profile of the recess.

18. The apparatus of claim 17, wherein:
an interior surface of the first channel is adapted to attachably receive an exterior surface of the first tube such that fluid communication can exist between the first channel and the first tube, and
an interior surface of the second channel is adapted to attachably receive an exterior surface of the second tube such that fluid communication can exist between the second channel and the second tube.

19. The apparatus of claim 17, wherein coupling the second connecting member and the first connecting member causes the exterior profile of the portion of the first connecting member to engage the interior profile of the recess of the second connecting member.

20. The apparatus of claim 17, wherein the first tube is adapted to be disposed externally from the patient nostril and a portion of the second tube is adapted to be disposed internally to the nostril of the patient.

* * * * *